(12) United States Patent
Neubauer et al.

(10) Patent No.: US 6,719,757 B2
(45) Date of Patent: Apr. 13, 2004

(54) DEVICE FOR ATTACHING AN ELEMENT TO A BODY

(75) Inventors: Timo Neubauer, München (DE); Matthias Brundobler, München (DE)

(73) Assignee: BrainLAB AG, Heimstetten (DE)

( * ) Notice: Subject to any disclaimer, the term of this patent is extended or adjusted under 35 U.S.C. 154(b) by 0 days.

(21) Appl. No.: 09/940,699

(22) Filed: Aug. 27, 2001

(65) Prior Publication Data

US 2002/0107518 A1 Aug. 8, 2002

(30) Foreign Application Priority Data

Feb. 6, 2001 (EP) .............................. 01102714
Feb. 27, 2001 (DE) ...................... 201 03 416 U

(51) Int. Cl.⁷ .............................................. A61B 17/00
(52) U.S. Cl. ....................................................... 606/53
(58) Field of Search .............................. 606/1, 54, 59, 606/53, 130, 96, 97; 600/429

(56) References Cited

U.S. PATENT DOCUMENTS

| 1,201,864 | A | * | 10/1916 | Overmeyer | 606/54 |
| 2,143,922 | A | * | 1/1939 | Longfellow | |
| 4,185,624 | A | * | 1/1980 | Gentile | |
| 6,203,543 | B1 | * | 3/2001 | Glossop | 606/61 |
| 6,241,735 | B1 | * | 6/2001 | Marmulla | 606/130 |
| 6,351,659 | B1 | * | 2/2002 | Vilsmeier | 606/130 |
| 6,450,978 | B1 | * | 9/2002 | Brosseau et al. | 600/595 |

FOREIGN PATENT DOCUMENTS

| DE | 297 04 393 U | 7/1997 |
| DE | 196 39 615 A | 4/1998 |
| DE | 200 16 635 U | 2/2001 |
| WO | 99 15097 A | 4/1999 |
| WO | 99 60939 A | 12/1999 |

* cited by examiner

Primary Examiner—David O. Reip
(74) Attorney, Agent, or Firm—Renner, Otto, Boisselle & Sklar, LLP

(57) ABSTRACT

The invention relates to a device for attaching an element securely to a body, in particular to a bone, wherein the device comprises at least one movable holding element enabling the device to be tensed against the body, as well as a system for attaching an element securely to a body comprising a connecting element which may be attached to the body.

9 Claims, 2 Drawing Sheets

DEVICE FOR ATTACHING AN ELEMENT TO A BODY

The invention relates to a device for attaching an element securely to a body, in particular fixing an element to a bone or joint in a minimally invasive manner.

In general, however, the device in accordance with the invention may also be used in open operations.

BACKGROUND OF THE INVENTION

Operations using navigated instruments, i.e. instruments which are detected with respect to their spatial position, need the position of a body structure to be determined as precisely as possible for targeted surgery using the instrument, from which to determine, for example, the relative position with respect to the instrument. For this purpose, so-called reference systems have to be attached, as securely and torsion-proof as possible, to a body structure, such as for example a bone or similar structure. Similar problems arise for example in the targeted irradiation of body regions.

SUMMARY OF THE INVENTION

It is the object of the present invention to propose a device for attaching an element securely to a body, in particular to a bone, which in a simple manner is able to ensure a secure connection between element and body. In particular, a device is to be proposed which is suitable for fixing an element to a body in a minimally invasive manner.

This object is solved by the device having the features in claim 1. Advantageous embodiments are given by the sub-claims.

The device in accordance with the invention, for attaching an element securely to a body, in particular to a bone, comprises at least one movable holding element, by which the device may be tensed against the body. The holding element/s is/are preferably movable relative to the body, and in particular may be driven into or out of the body, in order to tense the element against the body itself or against structures over the body, such as for example muscles and/or skin over a bone, through this relative movement. The at least one holding element, movable relative to the body, can thus, when suitably adjusted and/or positioned, fix an element firmly connected to the device in accordance with the invention rigidly to the body, such as for example a bone, by tensing against the bone itself and/or against a tissue over the bone.

The device is preferably attachable to a connecting element fixed to or in the body, in particular attachable to such a connecting element anchored in the body. If, for example, a nail or screw is inserted into a bone, the device in accordance with the invention can be attached to or arranged on the distal area of the nail or screw. The device in accordance with the invention can particularly preferably be fixed to the connecting element arranged on or in the body, which may be achieved, for example, by an adhesive, positive locking or frictional connection. Once the device in accordance with the invention has been fixed to the connecting element arranged on or in the body, the device in accordance with the invention may preferably be tensed by the at least one movable holding element. For this purpose, one or more holding elements may be moved relative to the device in the direction of the body, such as for example the bone or a tissue structure over it, in order to place the device in a firm positional relationship, no longer movable relative to the body. In accordance with a preferred embodiment, the device in accordance with the invention is positioned on the one hand by being fixed to a connecting element arranged on or in the body, and on the other hand by being tensed or supported by the at least one holding element movable relative to the body.

Advantageously, at least two movable holding elements, in particular four or six movable holding elements, are provided, which may be moved either individually or in combination with other or all holding elements to fix and/or tense the device in accordance with the invention.

The holding elements are preferably formed as rod or needle-shaped elements, so-called spikes, which may be driven into or out of the device in accordance with the invention, individually or together. This embodiment is particularly advantageous if the device is to be fixed to a bone, as the device in accordance with the invention may be tensed and/or fixed to the bone itself by driving out said spikes and placing the proximal area and/or the tips of the spikes onto the bone or even penetrating into the bone.

In another preferred embodiment, a plane element, such as for example a plate or a flat conical element, is provided as the movable holding element and is particularly suited to being tensed against tissue structures, so for example being tensed against the skin. Tips or spikes protruding from the element may also be provided in this respect, for better fixing.

The device in accordance with the invention is preferably attached to the at least one connecting element arranged on or in the body by fastening a nut or screw, such that the device in accordance with the invention can be clamped to the connecting element fixed in the body by moving the screw, for example.

A nut or screw is preferably also provided for moving the at least one movable holding element, such that the at least one movable holding element may be driven into or out of the device via a movement of the screw, in order to tense the device against the body or to detach the device, respectively.

In general, however, it is also possible, instead of screws, to provide other mechanisms which enable fixing and/or fastening, such as for example a locking mechanism or a tensing mechanism held by springs.

The element arranged on the body using the device in accordance with the invention is preferably a reference star, which may comprise one or more, in particular three, passive and/or active markers, and preferably can be altered with respect to its spatial position by a tensing mechanism. It is, for example, advantageous to arrange the device in accordance with the invention such that the element arranged on it can still be moved, and for instance aligned with respect to cameras and fastened, after the device has been fixed. In this respect, it is particularly advantageous to enable the element to move about at least axes, wherein the element, such as for example the reference star, can preferably be fixed in its aligned position, for example by screws.

The invention further relates to a system for attaching an element securely to a body using a connecting element which may be inserted into or attached to the body, respectively, such as for example a screw which may be screwed into a bone, or a nail, and using the device described above, arranged on said element.

It is also possible in accordance with the invention to rigidly fix an element, such as for example a reference system, to the body in a minimally invasive manner using basic connecting elements commonly available on the market, such as for example Schantz screws, Kirschner wires, Steinmann nails, etc., or pedical screws which may be inserted into the spine, osteo-synthesis screws used in plates for bone fractures or also implants arranged on a body structure. Thus in accordance with the invention, a reference star for example can be attached torsion-proof to a body structure using a single element, such as for example a single screw. In general, however, it is also possible more than just one such element, or to use the device in operations which are not minimally invasive.

In the following, the invention will be described by way of two preferred example embodiments.

DETAILED DESCRIPTION

Figure 1:
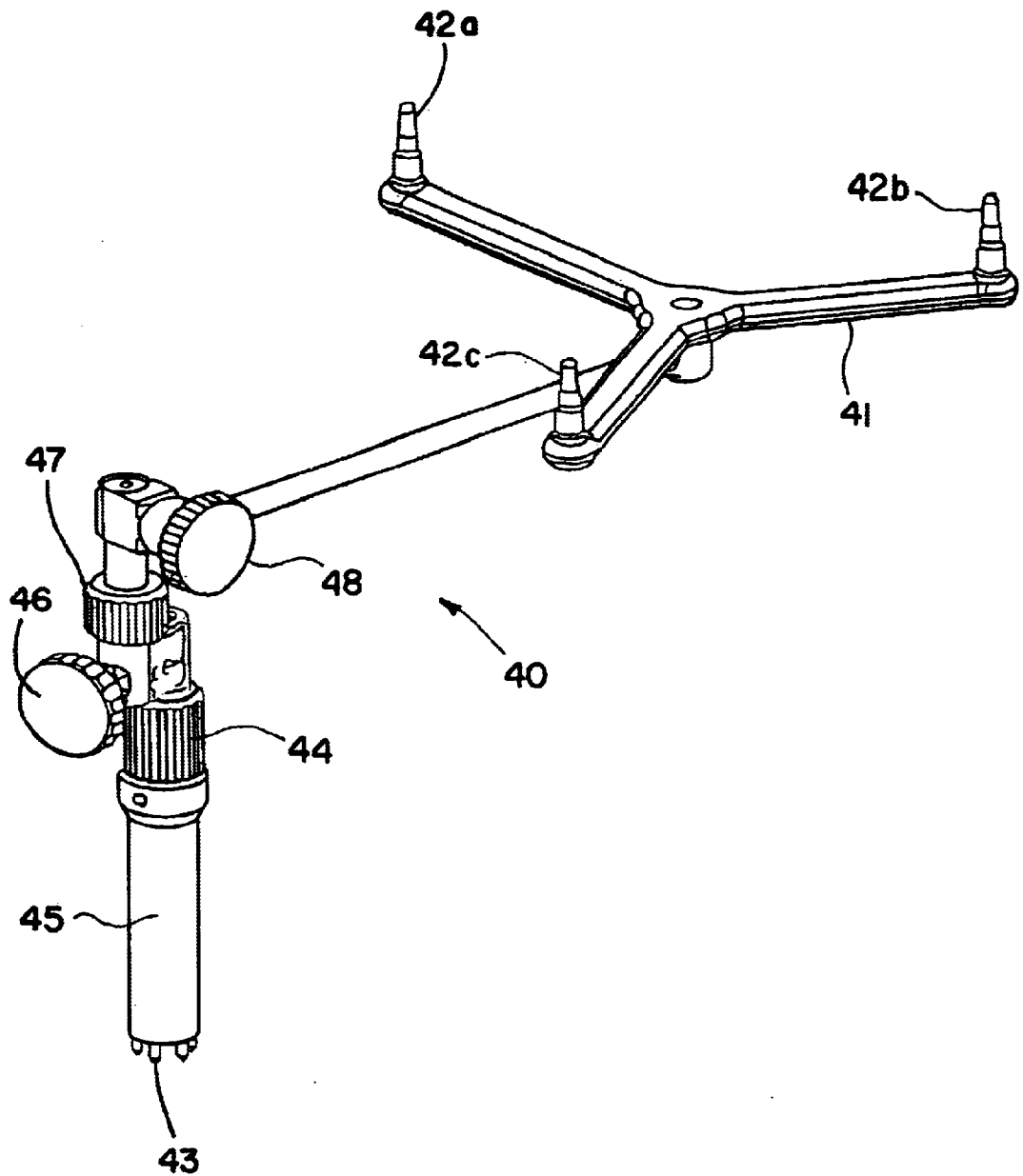
FIG. 1 a device in accordance with the invention in a first embodiment.

FIG. 1 shows a first embodiment of the device 40 in accordance with the invention, with which a reference star 41 with mountings 42a to 42c arranged on it may be fixed to a bone or other structure, for attaching reflecting markers (not shown) in a defined positional relationship. The reference star 41, fixed for example to a bone, may serve as a reference system for navigating and/or positioning other devices, such as for example pedical screws which may be inserted into the spine, implants for plates and/or screws, also implants arranged or to be arranged on or in a body structure.

The spikes 43 shown on the underside of the device 40, which are connected to the casing 45, may be driven in or out by turning the nut 44. If for example a rod, such as for example a Schantz screw or a Kirschner wire, is inserted into a bone to attach the device 40, the device 40 can then be attached to said rod arranged in the bone using the casing 45. The screw 46 serves to fix the device 40 to said rod. Once the device 40 has been fixed by means of the screw 46, the nut 44 may be turned in order to move the spikes 43 downwards and so tense the device 40 with respect to the bone or another element, such as for example skin or elements arranged on the skin. A reference star 41 can thus be connected securely and non-shiftably to just a single rod in a bone, since it is possible to tense the device 40 via the spikes 43 which may be driven in or out. The position of the reference star 41 may be altered by means of the screws 47 and 48 by turning them about two axes.

Figure 2:
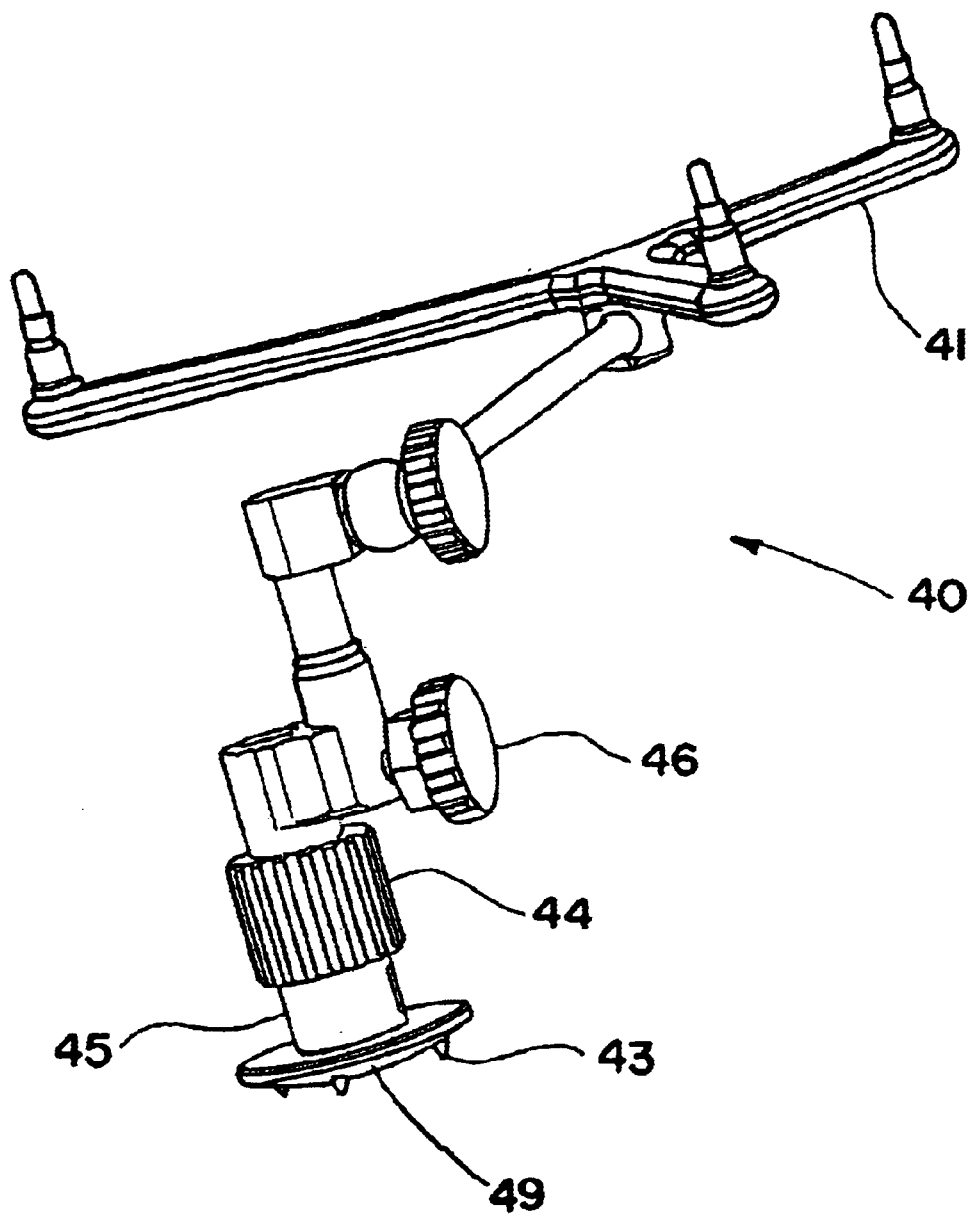
FIG. 2 a device in accordance with the invention in a second embodiment.

FIG. 2 shows a second embodiment of a device 40 for securely attaching a reference star 41, wherein the spikes 43 are arranged on a supporting surface 49 and may be moved downwards with the surface 49 in order to so tense the device 40 firmly against the surface of the skin, or by inserting the spikes 43 into soft tissues.

In general, then, an element, such as for example a rod, is in accordance with a preferred embodiment of the invention inserted into a bone and the device 40 is attached to the rod arranged on the bone using the casing 45, wherein the screw 46 serves to fix the device 40 to said rod. Once the device 40 has been fixed by means of the screw 46, the nut 44 may be turned in order to drive out the casing 45 with the spikes 43 arranged on it downwards and so tense the device 40 with respect to the bone or, in the embodiment shown in FIG. 2 with respect to the skin or other elements arranged in the skin, in soft tissues, on the skin, on soft tissues or on bones. The reference star 41 can thus be connected securely, non-shiftably and torsion-proof to just a single rod in a bone. In this way, the device 40 may be tensed via the casing 45 which may be driven in or out and on which the spikes 43 are arranged, due to the resistance to being drawn out of the rod inserted into the bone, which thus enables a high tensile stability.

European Patent Application No. 01 102 714.1 filed Feb. 6, 2001 and German Utility Model Application No. 201 03 416.6 filed Feb. 27, 2001 are hereby incorporated herein by referenced in their entireties.

What is claimed is:

1. A device (40) for attaching a reference star (41) comprising at least one of (i) passive and (ii) active markers securely to a body, said device (40) comprising:

a first element (46) for attaching the device (40) to an associated connecting element arranged on the body; and at least one movable holding element (43) enabling the device (40) to be tensed against the body.

2. The device as set forth in claim 1, wherein the device is tensed by moving the at least one holding element (43) relative to the connecting element arranged on the body.

3. The device as set forth in claim 1, wherein at least two movable holding elements (43) are provided.

4. The device as set forth in claim 1, wherein the movable holding element (43) includes at least one of (i) a rod and (ii) a needle-shaped element.

5. The device as set forth in claim 1, wherein the movable holding element includes at least one of (i) a plane and (ii) a conical element (49).

6. The device as set forth in claim 1, wherein the first element includes at least one of (i) a screw and (ii) a nut (46) for fixing the device to the associated connecting element arranged on the body.

7. The device as set forth in claim 1, further comprising at least one of (i) a nut and (ii) a screw (44) for moving the at least one holding element (43).

8. The device as set forth in claim 1, further comprising an adjusting device (47, 48) for adjusting the position of the reference star (41) relative to the device.

9. The device as set forth in claim 1, wherein the connecting element is attached onto or inserted into a bone, said connecting element including at least one of (i) a rod, (ii) a screw, (iii) a wire (iv) a nail.

\* \* \* \* \*